United States Patent
Seleznev et al.

(10) Patent No.: US 10,241,101 B2
(45) Date of Patent: Mar. 26, 2019

(54) METHOD AND APPARATUS FOR DETERMINING PERMITTIVITY OF ROCK MATRIX

(71) Applicant: Schlumberger Technology Corporation, Sugar Land, TX (US)

(72) Inventors: Nikita Seleznev, Cambridge, MA (US); Kamilla Fellah, Brookline, MA (US); Bastien Fournie, Pamiers (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 835 days.

(21) Appl. No.: 14/604,108

(22) Filed: Jan. 23, 2015

(65) Prior Publication Data

US 2015/0212228 A1    Jul. 30, 2015

Related U.S. Application Data

(60) Provisional application No. 61/931,118, filed on Jan. 24, 2014.

(51) Int. Cl.
*G01V 3/38*    (2006.01)
*G01N 33/24*   (2006.01)

(52) U.S. Cl.
CPC .................... *G01N 33/241* (2013.01)

(58) Field of Classification Search
CPC ........... G01V 3/38; G01V 3/02; G01N 33/241
USPC ............................................................ 702/7
See application file for complete search history.

(56) References Cited

U.S. PATENT DOCUMENTS

| | | | | |
|---|---|---|---|---|
| 4,920,792 A | * | 5/1990 | DiFoggio | G01N 15/0893 208/188 |
| 4,996,421 A | * | 2/1991 | Rai | G01N 21/3563 250/253 |
| 2007/0061082 A1 | * | 3/2007 | Seleznev | G01V 3/26 702/11 |
| 2007/0188177 A1 | * | 8/2007 | Troxler | G01N 22/00 324/643 |
| 2013/0066605 A1 | * | 3/2013 | Li | E21B 49/06 703/2 |

OTHER PUBLICATIONS

Ulaby, F. T. et al., "Microwave Dielectric Properties of Dry Rocks", IEEE Transactions on Geoscience and Remote Sensing, May 1990, 28(3), pp. 325-336.
Polder, D. et al., "The Effective Permeability of Mixtures of Solids," Physica, Aug. 1946,12(5), pp. 257-271.
Birchak, J. R. et al., "High Dielectric Constant Microwave Probes for Sensing Soil Moisture," Proceedings of the IEEE, Jan. 1974, 62(1), pp. 93-98.
Looyenga, H., "Dielectric Constants of Heterogeneous Mixtures", Physica, Mar. 1965, 31(3), pp. 401-406.

(Continued)

*Primary Examiner* — Yoshihisa Ishizuka
(74) *Attorney, Agent, or Firm* — Michael Dae

(57) ABSTRACT

A method for determining permittivity of a rock formation mineral matrix includes measuring a permittivity of a sample of the rock. A fractional volume of pore space in the sample is determined. A mixing law and a permittivity of a fluid filling the pore space are used to determine the permittivity of the formation mineral matrix from the measured permittivity.

21 Claims, 8 Drawing Sheets

(56) References Cited

OTHER PUBLICATIONS

Courtney, W. E., "Analysis and Evaluation of a Method of Measuring the Complex Permittivity and Permeability of Microwave Insulators", IEEE Transactions on Microwave Theory and Techiques, Aug. 1970,18(8), pp. 476-485.
Krupka, J., "Frequency Domain Complex Permittivity Measurements at Microwave Frequencies", Measurement Science Technology, Jun. 2006, 17, pp. R55-R70.
Krupka, J. et al., "A Dielectric Resonator for Measurements of Complex Permittivity of Low Loss Dielectric Materials as a Function of Temperature", Measurement Science Technology, Jul. 20, 1998, 9, pp. 1751-1756.
Seleznev, N. et al., "Applications of the Dielectric Dispersion Logging to Oil-Shale Reservoirs", Society of Petrophysicists and Well-Log Analysts, presented at SPWLA Annual Logging Symposium, Colorado Springs, CO, May 14-18, 2011, pp. 1-16.
Robinson, D. A., "Measurement of the Solid Dielectric Permittivity of Clay Minerals and Granular Samples Using a Time Domain Reflectometry Immersion Method", Vadose Zone Journal, May 2004, 3(2), pp. 705-713.
Dunsmuir R. et al., 1946, "A Method for the Measurement of the Dielectric Properties of Liquids in the Frequency Range 600-3200 Mc./sec. (50-9.4 cm).", Jan. 25, 1946, The London, Edinburgh, and Dublin Philosophical Magazine and Journal of Science, Series 7, 37 (274) 747-756.

* cited by examiner

METHOD AND APPARATUS FOR DETERMINING PERMITTIVITY OF ROCK MATRIX

CROSS-REFERENCE TO RELATED APPLICATIONS

This application claims benefit of U.S. provisional patent application Ser. No. 61/931,118, filed Jan. 24, 2014, which is herein incorporated by reference.

BACKGROUND

1. Technical Field

This disclosure is related to the field of determining dielectric properties of materials. In relation to measurements of subsurface rock formation properties, the disclosure pertains to dielectric measurements of such formations and dielectric well log interpretation.

2. Background Information

This section is intended to introduce the reader to various aspects of art that may be related to various aspects of the subject matter described and/or claimed below. This discussion is believed to be helpful in providing the reader with background information to facilitate a better understanding of the various aspects of the present disclosure. Accordingly, it should be understood that these statements are to be read in this light, not as admissions of prior art.

Formation water content in porous subsurface formations is one of the petrophysical quantities provided by dielectric measurements (e.g., obtained by well logging) of such formations. However, to determine formation water content from the formation dielectric measurements, the formation rock matrix permittivity must be known. Uncertainty in the rock matrix permittivity values translates into uncertainty in the formation water content estimate, which is especially important in low-porosity formations or complex lithologies (rock matrix mineral compositions). Generally, the matrix permittivity values are not well known for a number of formation minerals and can also vary for the same type of mineral if it forms part of different formations.

An approach for measuring permittivity of solid powder phase based on "no-contrast conditions" has been proposed that can also be applied to rock formation materials. See Robinson, D. A., 2004, "*Measurement of the solid dielectric permittivity of clay minerals and granular samples using a TDR immersion method,*" Vadose Zone Journal, 3 (2), pp. 705-713. The approach described in the foregoing publication includes a series of measurements on a powder filled with variable permittivity liquids. When the measured permittivity of the powder/liquid mixture equals the permittivity of the saturating liquid, so-called "no contrast" conditions are met. Under such no contrast conditions, the permittivity of the solid powder phase equals the permittivity of the saturating fluid. Published methodologies required a demanding measurement technique that had to be practiced before reliable data could be obtained, which may make such methods impractical.

Another implementation of the no-contrast methodology involving measurements on liquid/powder mixtures was based on measurements made using a capacitive measurement cell. Capacitive measurement cells may make inferior accuracy measurements compared with other available techniques and may also be limited in measurement frequency span. Such limitations may not allow the measurement to be easily extended to 1 gigahertz (GHz) range, which is important in dielectric well logging for determination of water-filled porosity. This is because some dielectric well logging instruments make measurements in the 1 GHz frequency range.

Other attempts to study dielectric properties of dry rocks included utilization of a dielectric probe. Use of such probes is a fast and convenient measurement technique, but also has lesser accuracy as compared to some other techniques. Generally, it requires good contact between the sample and the probe surfaces, and is only sensitive to a part of the sample volume which is adjacent to the probe. See Ulaby, T. F., Bengal, T. H., Dobson, C. M., East, J. R., Garvin, J. B., and Evans, D. L., 1990, "*Microwave Dielectric Properties of Dry Rocks*", IEEE Trans. On Geoscience and Remote Sensing, vol. 28, No. 3, 325-336.

SUMMARY

A summary of certain embodiments disclosed herein is set forth below. It should be understood that these aspects are presented merely to provide the reader with a brief summary of certain embodiments and that these aspects are not intended to limit the scope of this disclosure. Indeed, this disclosure may encompass a variety of aspects that may not be set forth in this section.

A method according to one aspect for determining permittivity of a rock formation mineral matrix includes measuring a permittivity of a sample of the rock formation. A fractional volume of pore space in the sample is determined. A mixing law and a permittivity of a fluid filling the pore space are used to determine the permittivity of the formation mineral matrix from the measured permittivity.

Again, the brief summary presented above is intended to familiarize the reader with certain aspects and contexts of embodiments of the present disclosure without limitation to the claimed subject matter. Other aspects and advantages will be apparent from the description and claims that follow.

BRIEF DESCRIPTION OF THE DRAWINGS

The present disclosure is best understood from the following detailed description when read with the accompanying figures. It is emphasized that, in accordance with standard practice in the industry, various features are not necessarily drawn to scale. In fact, the dimensions of various features may be arbitrarily increased or recued for clarify of discussion.

DETAILED DESCRIPTION

Figure 1:
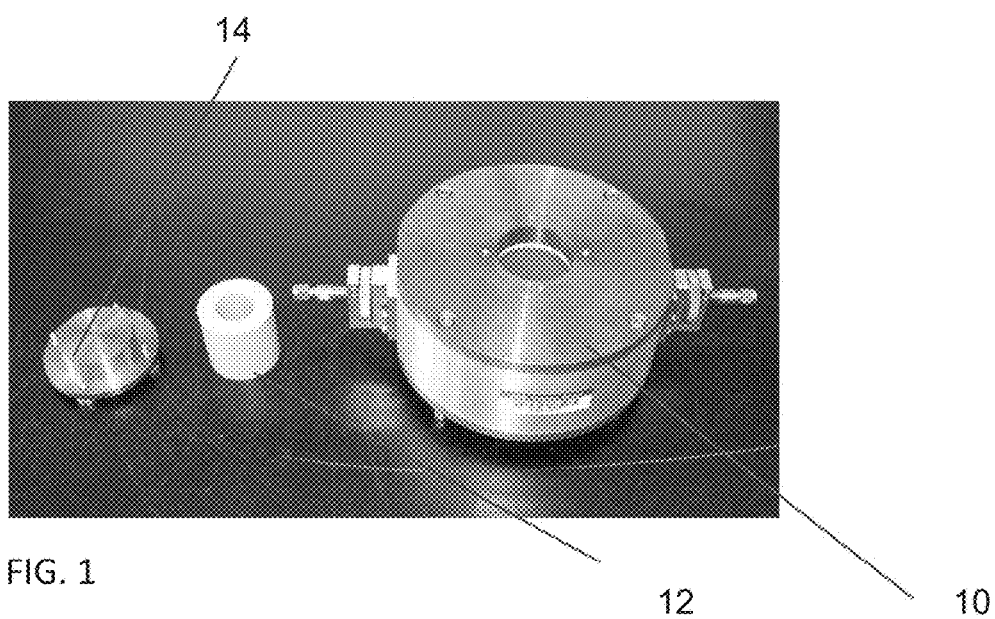
FIG. 1 shows an example resonator for making permittivity measurements on solid samples.

One or more specific embodiments of the present disclosure are described below. These embodiments are merely examples of the presently disclosed techniques. Additionally, in an effort to provide a concise description of these embodiments, all features of an actual implementation may not be described in the specification. It should be appreciated that in the development of any such implementation, as in any engineering or design project, numerous implementation-specific decisions are made to achieve the developers' specific goals, such as compliance with system-related and business-related constraints, which may vary from one implementation to another. Moreover, it should be appreciated that such development efforts might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The embodiments discussed below are intended to be examples that are illustrative in nature and should not be construed to mean that the specific embodiments described herein are necessarily preferential in nature. Additionally, it should be understood that references to "one embodiment" or "an embodiment" within the present disclosure are not to be interpreted as excluding the existence of additional embodiments that also incorporate the recited features.

1. Measurement of Permittivity on Solid Core Samples

Formation core material is often available in a form of solid cylindrical "plugs" that are, for example, 1.5 inches in diameter and 1.5 inches long. Thus, it is desirable to have a non-destructive methodology for measurements of the matrix permittivity on these commonly available samples. In this section an experimental methodology is described for dielectric measurements on such solid cylindrical samples and estimation of the permittivity of the solid phase.

The permittivity value measured on a dry rock sample plug differs from the permittivity of the rock matrix due to the presence of air-filled porosity unless the rock sample is tight (i.e., has very low porosity). The permittivity of air is lower than the permittivity of rock matrix and, therefore, the measured permittivity of the dry rock is lower than the permittivity of rock matrix. Thus, a correction to the measured permittivity of dry rock plug may be applied to estimate permittivity of the solid rock mineral phase of a dry rock sample plug. Such correction may be performed using a mixing law and porosity measurements (measurements of fractional volume of void or pore space in the rock sample). Various dielectric mixing laws described below demonstrate how this technique may be applied.

A number of mixing laws have been proposed for description of the dielectric properties of mixture, such as rock matrix and air-filled porosity. Some of the commonly utilized mixing laws are listed below:

Maxwell-Garnett mixing formula:

$$\frac{\varepsilon_{eff} - \varepsilon_b}{\varepsilon_{eff} + \varepsilon_b} = \sum_{n=1}^{N} \phi_n \frac{\varepsilon_n - \varepsilon_b}{\varepsilon_n + 2\varepsilon_b} \quad (2)$$

Where $\varepsilon_n$—permittivity of the inclusion (void or pore space) phase "n", $\phi_n$—volumetric fraction of the inclusion phase "n", $\varepsilon_b$—permittivity of the background (rock mineral or matrix) phase, $\varepsilon_{eff}$—effective permittivity of the rock sample.

The Maxwell-Garnett model does not treat the host and inclusions equally. An alternative approach that treats all phases symmetrically is known as the Effective Medium Approximation (EMA) and is given by the expression:

$$\sum_{n=1}^{N} \phi_n (\varepsilon_n - \varepsilon_{eff}) / (\varepsilon_n + 2\varepsilon_{eff}) = 0 \quad (3)$$

Other mixing laws may include the Polder-van Santen mixing formula or the Bottcher mixing formula:

$$\frac{\varepsilon_{eff} - \varepsilon_o}{3\varepsilon_{eff}} = \sum_{n=1}^{N} \phi_n \frac{\varepsilon_n - \varepsilon_o}{\varepsilon_n + 2\varepsilon_{eff}} \quad (4)$$

Another set of mixing formulas is based on the family of exponential models of degree "m". A general representation of an exponential mixing for a multi-component composite may be provided by the expression:

$$\varepsilon_{eff}^{1/m} = \sum_{n=1}^{N} \phi_n \varepsilon_n^{1/m} \quad (5)$$

where $\phi_n$ is the volumetric fraction of the inclusion (porosity) phase with permittivity $\varepsilon_n$.

The Arithmetic Average (Volumetric) Mixing Formula may be given by the expression:

$$\varepsilon_{eff} = \sum_{n=1}^{N} \phi_n \varepsilon_n \quad (6)$$

The volumetric formula averages the dielectric constant in a direct proportion to the volumetric fractions of the inclusion (porosity) phases.

The Harmonic Average Mixing Formula may be expressed as:

$$\varepsilon_{eff}^{-1} = \sum_{n=1}^{N} \phi_n \varepsilon_n^{-1} \quad (7)$$

Eq. (7) is a special case of Eq. (5) with m=(−1).

Mixtures described by the harmonic average and the arithmetic average are two extreme cases possessing the lowest possible and the highest possible permittivity for a given volume fraction of mixture components. These equations form so-called "Wiener bounds", which limit the permittivity of an anisotropic mixture with lossless components.

The Complex Refractive Index Formula is given by the expression:

$$\varepsilon_{\it eff}^{1/2} = \sum_{n=1}^{N} \phi_n \varepsilon_n^{1/2} \tag{8}$$

As evident from the name Eq. (8) averages the refractive indices of the constituents of a sample. This mixing law can also be found under the name of Beer's (or Birchak's) mixing formula. It is a special case of Eq. (5) with m=2, and it assumes that the total transit time of an electromagnetic pulse propagating in a composite medium is given by the sum of the transit times of the constituents.

The Looyenga-Landau-Lifshiz (LLL) Mixing Formula is given by the expression:

$$\varepsilon_{\it eff}^{1/3} = \sum_{n=1}^{N} \phi_n \varepsilon_n^{1/3} \tag{9}$$

The LLL mixing formula is a special case of Eq. (5) with m=3. The derivation of the LLL formula assumes either low dielectric contrast between different inclusion phases, or a small volume fraction of the inclusions with higher dielectric contrast.

Lichtenecker's Mixing Formula may be given by the expression:

$$\ln(\varepsilon_{\it eff}) = \sum_{n=1}^{N} \phi_n \ln(\varepsilon_n) \text{ or } \varepsilon_{\it eff} = \prod_{n=1}^{N} \varepsilon_n^{\phi_n} \tag{10}$$

Eq. (10) is an empirical formula and is a special case of Eq. (5) when m→∞.

Any of the above described dielectric mixing laws can be utilized to calculate permittivity of dry rock matrix using the measurements of the effective permittivity of a dry rock sample and rock porosity, although the above examples are not limiting as other mixing laws may be used. An example technique based on the CRIM (Complex Refractive Index Method) mixing law will be explained further below, but any other mixing law can also be used to estimate the permittivity of the solid phase. The rock matrix permittivity of a dry rock sample may be estimated from the CRIM mixing law as follows:

$$\varepsilon_{\it matrix} = \left( \frac{\sqrt{\varepsilon_{\it rock}} - \phi \sqrt{\varepsilon_{\it air}}}{1-\phi} \right)^2 \tag{12}$$

Where $\varepsilon_{\it rock}$ is the effective permittivity measured on dry core plug, $\varepsilon_{\it air}$ is the permittivity of air and $\phi$ is the rock porosity. The measurements of the total rock porosity are a common part of core analysis and such measurement techniques are well described in the literature on core analysis.

The permittivity measurements of solid plug samples can be carried out with any available permittivity measurement technique. Good results may be obtained with a laboratory measurement instrument such as the dielectric resonator described below. In addition, the dielectric resonator operates at microwave frequencies in the same frequency range as commonly known wellbore dielectric logging tools.

Resonant methods are widely utilized due to their high accuracy. The resonant methods for material characterization are utilizing the effect of microwave resonance. Resonance is related to energy exchange, and electromagnetic resonance can be taken as a phenomenon when electric energy and magnetic energy periodically totally exchange one to another. The frequency at which the resonance occurs called the "resonant frequency".

Resonant methods generally include a resonator method and a resonant-perturbation method. In the resonator method, the sample serves as a resonator or a key part of a resonator in a measurement circuit and the properties of the sample are derived from the resonant properties of the resonator. The resonant-perturbation method is based on resonant-perturbation theory. For a resonator with given electromagnetic boundaries, when part of the electromagnetic boundary condition is changed by introducing a sample, its resonant frequency and quality factor will also be changed. From the changes of the resonant frequency and quality factor, the properties of the sample can be derived. It should be clearly understood that measuring permittivity using a dielectric resonator is only one possible implementation of measurement techniques according to embodiments of the present disclosure. It should be clearly understood that any other permittivity measurement technique known in the art may be used to determine permittivity of samples in accordance with embodiments of the present disclosure.

In testing a technique for measuring permittivity of dry rock plug samples, a 1.085 GHz $TE_{01\delta}$ mode dielectric resonator was used. Such resonators may be obtained, for example, from QWED Company, Warsaw, Poland. See Krupka, J., Derzakowskiz, K., Riddlex, B., and Baker-Jarvis, J., 1998, *"A Dielectric Resonator for Measurements of Complex Permittivity of Low-Loss Dielectric Materials as a Function of Temperature"*, Meas. Sci. Technol., 9, pp. 1751-1756 for a more complete description of the foregoing resonator. Referring to FIG. 1, the resonator is shown at 10, a sample holder at 12 and a resonator cover at 14. This dielectric resonator may be better suitable for measurements on solid cylindrical plug samples. By way of example only, power to operate the resonator and a measurement analyzer for the resonator may be provided by a network analyzer sold under model number E5071C by Agilent Technologies, 5301 Stevens Creek Blvd., Santa Clara, Calif. 95051. The solid rock sample may be cut in a cylindrical shape with the sample height and diameter being about 38.0 mm (1.5 inches).

A single set of measurements with the dielectric resonator includes determination of the resonant frequency and the quality factor. The quality factor is defined as:

$$Q_0 = 2 \cdot \pi \frac{W_t}{T_0 W_d} = \omega_0 \frac{W_t}{W_d} \tag{13}$$

Where $W_t$ is the total energy storage in the cavity, $W_d$ is the average energy dissipation within the cavity and $T_0$ is the resonance period.

In case of a hollow metallic cavity filled with a lossless dielectric medium the energy dissipation is caused by the cavity wall. This loss is determined via measurements of the quality factor of the empty dielectric resonator. Presence of a sample in the dielectric resonator leads to a change in the resonant frequency and the measured quality factor due to additional dissipation of the energy in the sample.

Determination of the complex permittivity of the solid cylindrical samples requires two sets of measurements of the resonance frequencies and quality factors: (i) the empty resonator; and (ii) the resonator with a sample. Measurements of the quality factor were carried out using the 3 dB resonance curve bandwidth of a weakly coupled resonator. A description of how to obtain complex permittivity from resonator measurements is described, for example, in Jerzy Krupka, "Frequency domain complex permittivity measurements at microwave frequencies," Meas. Sci. Technol. 17 (2006) R55-R70.

In testing the foregoing technique using the above described dielectric resonator, fourteen rock samples were analyzed. Before the measurements were made, the samples were oven-dried at 100° C. for 24 hours under vacuum to remove residual water.

The results of the dielectric measurements, routine core analysis and the matrix permittivity values are summarized in Table 1 below. Column 2 in Table 1 shows porosity values of the solid rock samples, column 3 shows the dielectric constant measured on the dry rock samples, and column 4 gives the matrix permittivity of the solid rock phase determined from the porosity measurement and the effective permittivity of the plug.

Figure 2:
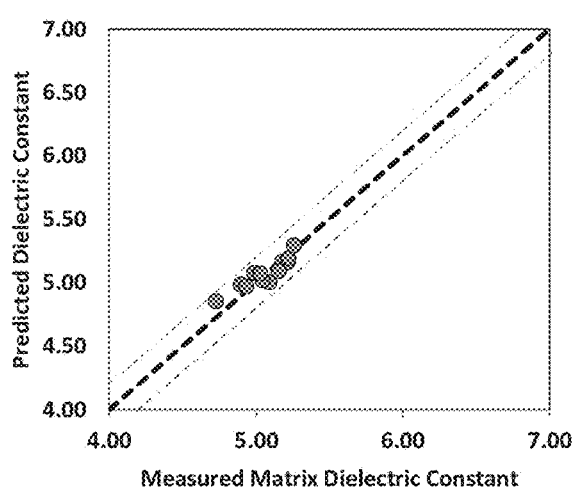
FIG. 2 shows a graph of estimated core matrix permittivity from its mineralogical content compared with measured values.

In addition, the mineralogical content of the core samples was analyzed. The mineral permittivity end-points were verified by estimating the core matrix permittivity from its mineralogical content and comparing with the measured values as shown in FIG. 2. Good comparison between the measured and predicted values confirms the mineral permittivity end-points.

In other embodiments, solid porous samples can be carried saturated with liquids to reduce the dielectric constant between the medium filling the rock porosity and the rock matrix. Such procedure may improve the accuracy of the matrix permittivity estimate as described below in this disclosure in the section on powder measurements.

TABLE 1

MATRIX PERMITTIVITY MEASUREMENTS AND ROUTINE
CORE ANALYSIS RESULTS FOR ROCK SAMPLES

| Sample No | Porosity (%) | Measured Permittivity Solid Plug | Matrix Permittivity |
|---|---|---|---|
| 1 | 19 | 3.80 | 4.7 |
| 2 | 16 | 4.24 | 5.1 |
| 3 | 16 | 4.17 | 5.0 |
| 4 | 17 | 4.03 | 4.9 |
| 5 | 17 | 4.05 | 4.9 |
| 6 | 15 | 4.21 | 5.0 |
| 7 | 16 | 4.10 | 4.9 |
| 8 | 18 | 3.95 | 4.9 |
| 9 | 17 | 4.20 | 5.2 |
| 10 | 17 | 4.22 | 5.2 |
| 11 | 17 | 4.27 | 5.2 |
| 12 | 19 | 4.14 | 5.2 |
| 13 | 19 | 4.11 | 5.2 |
| 14 | 21 | 4.08 | 5.3 |

TABLE 1-continued

MATRIX PERMITTIVITY MEASUREMENTS AND ROUTINE
CORE ANALYSIS RESULTS FOR ROCK SAMPLES

2. Determination of the Matrix Permittivity on Dry Powder:

The permittivity of a dry powder solid phase may be determined with methodology similar to the permittivity measurements used on dry solid plug or core samples. The foregoing requires measurement of the powder permittivity and porosity. The measurement of the powder permittivity can be carried out using a $TE_{01\delta}$ mode dielectric resonator as described above or any other technique for dielectric measurements. Measurements of the powder porosity can be based on the powder grain density, weight and bulk volume or any other suitable technique.

A series of measurements at various compaction levels may be carried out for a powdered sample and all or a subset of the experimental data is simultaneously fitted using a mixing law. Simultaneous analysis of multiple measurements ensures more reliable determination of the matrix permittivity value.

Figure 3:
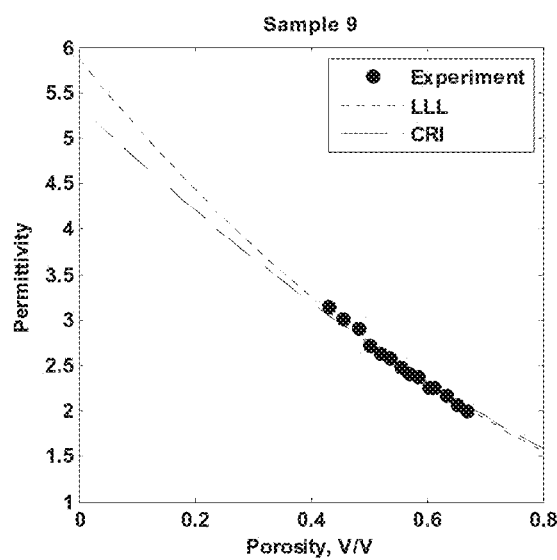
FIG. 3 shows a graph of the measured permittivity of dry powders at different compaction stages.

Test measurements on a rock powder at different compaction stages obtained with a $TE_{01\delta}$ mode dielectric resonator are shown in FIG. 3. The measurements were obtained at different powder compaction stages. As powder gets more compacted, the air-filled porosity of the powder is reduced and the effective permittivity of the powder increases.

The permittivity of the solid phase may be obtained from any single compaction stage using correspondent dielectric and porosity measurements and applying a mixing law as described above. Alternatively, the permittivity of the solid powder phase can be determined from simultaneous fitting of the powder permittivity values measured at various compaction stages as shown in FIG. 3. The mixing laws used in fitting include, but are not limited to CRIM and LLL laws. The permittivity may be determined based on one selected mixing law or by averaging the results obtained using several different mixing laws.

In other embodiments, the matrix permittivity may be determined based on extrapolation of empirical dependence of the various compaction measurement to zero porosity value using e.g., polynomial or any other type of curve fitting. Intersection of the permittivity curve at zero porosity provides the value of the matrix permittivity.

Figure 4:
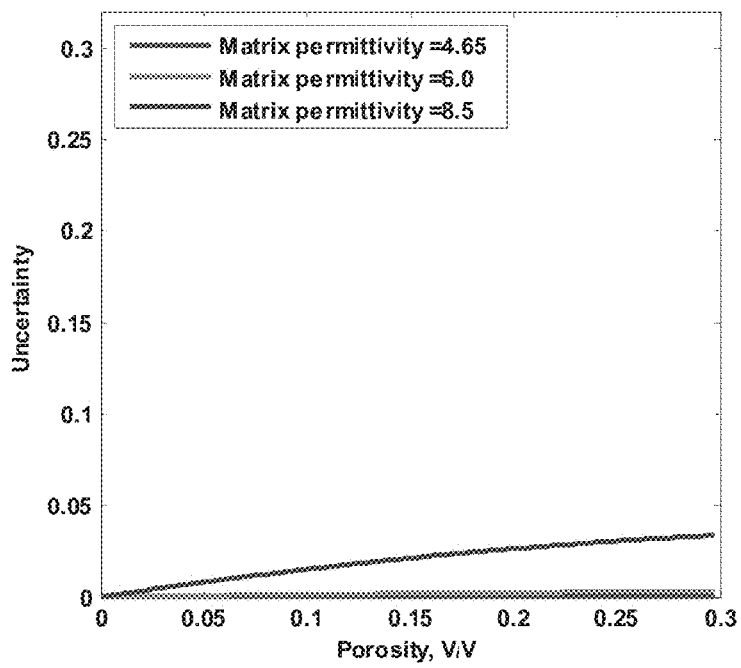
FIG. 4 shows a graph of dependence of rock matrix permittivity uncertainty due to the choice of mixing law where the rock porosity is filled with material with permittivity of 5.
Figure 5:
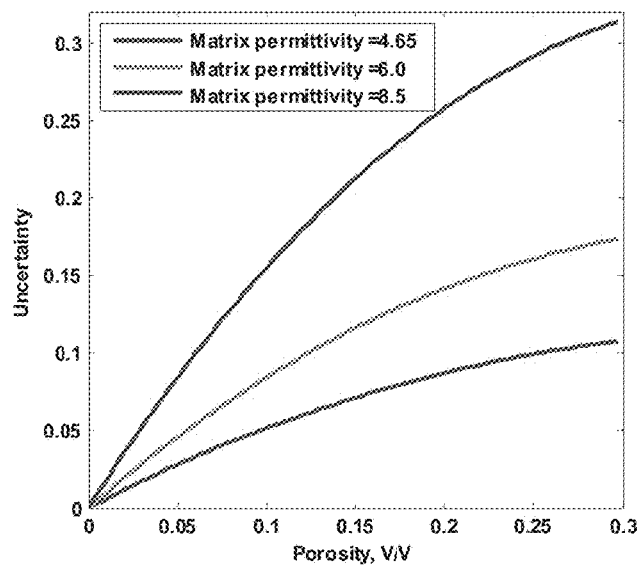
FIG. 5 shows a graph of dependence of the rock matrix permittivity uncertainty due to the choice of a mixing law on samples with air-filled rock porosity.

Rock powders may have higher porosity than most solid cores. This leads to an increase in the correction for air-filled porosity and associated uncertainty in the determined matrix permittivity. A convenient way to reduce this effect is to fill powders with a dielectric material with a permittivity higher than that of air. Such procedure may reduce the dielectric contrast between the powder and the filling material and consequently reduces the required correction. An illustration of this effect is shown in FIG. 4 where porosity is assumed to be filled with a material with permittivity equal to 5. The vertical axis shows difference between CRIM and LLL mixing law predictions for rocks with different porosity and matrix permittivity. Comparison with a similar analysis for air-filled porosity in FIG. 5 shows that increases in the permittivity of the filler leads to a significant reduction in the uncertainty of predictions using different mixing laws. The uncertainty reduces proportionally to the decrease in the permittivity difference between the filler and the solid phase of the powder.

For measuring permittivity of powders it is practical to use liquids as a filler material. To ensure minimization of the dielectric contrast between the powder and liquid, several liquids with different permittivities can be used that either sequentially fill the same sample or saturate several separate samples of the same rock powder.

Figure 6:
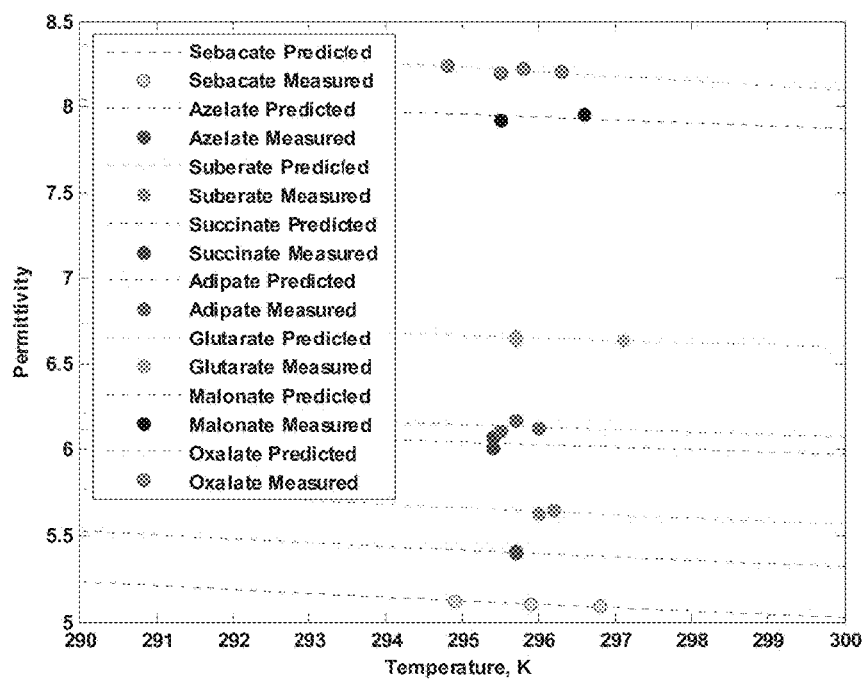
FIG. 6 shows a graph of a comparison between predicted and measured permittivity values for various diethyl fluids.

The foregoing technique was tested using diethyl liquids, but any other type of liquid with appropriate permittivity values may be used. Dielectric measurements obtained using a $TM_{010}$ mode dielectric resonator on pure diethyl liquids is shown in the graph of FIG. 6. Such resonators may also be obtained from QWED Company.

In other examples, liquids with various permittivities can be obtained by mixing two liquids that have permittivities higher and lower than the required permittivity range. By mixing two "end-point" liquids in different proportions one can obtain a mixture with any intermediate required permittivity.

In testing the foregoing technique, measurements on liquids and liquid/powder mixtures were made with a $TM_{010}$ mode dielectric resonator. Any other measurement technique may be also be used that provides the permittivity of such samples.

The foregoing dielectric resonator cavity has a cylindrical shape with a cylindrical sample being placed in its center. A quartz tube is filled with liquid (or powder or mixture of both) so that the sample fills the entire length of the tube inside the resonator cavity and also extends beyond its dimensions. The influence of the quartz tube on the measurements is eliminated by making measurements of the resonance frequency and quality factor of an empty quartz tube inserted in the resonator cavity. Next the quartz tube is filled with liquid sample and measurements of the resonance frequency and quality factor are repeated. Combination of these two measurements allows determination of the samples dielectric constant and loss tangent.

Figure 7:
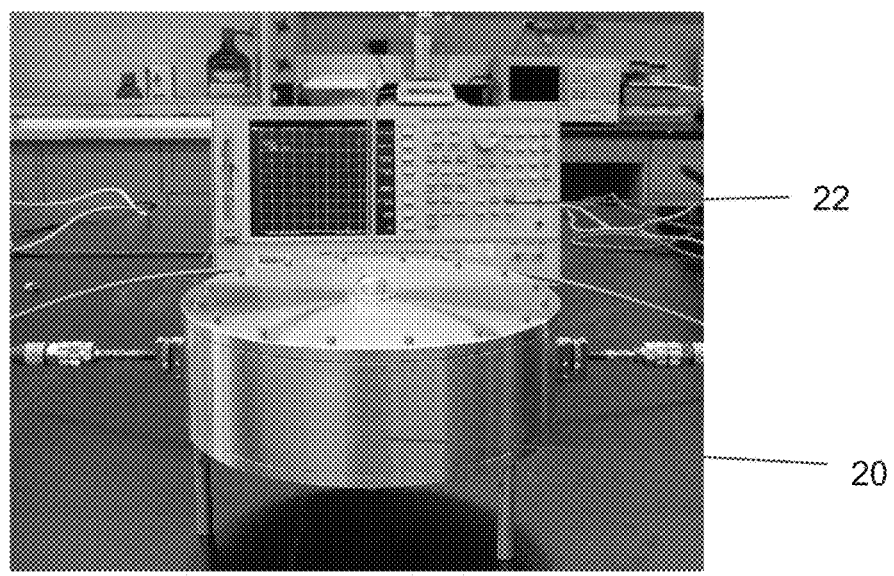
FIG. 7 shows an example $TM_{010}$ resonator connected to a network analyzer.

A representation of the $TM_{010}$ mode dielectric resonator 20 operating at 960 MHz with inserted quartz tube and connected to a network analyser 22 is shown in FIG. 7. The $TM_{010}$ mode resonator used in the present example was designed to conduct measurement at approximately 1 GHz, which is a frequency used in dielectric well logging.

Figure 8:
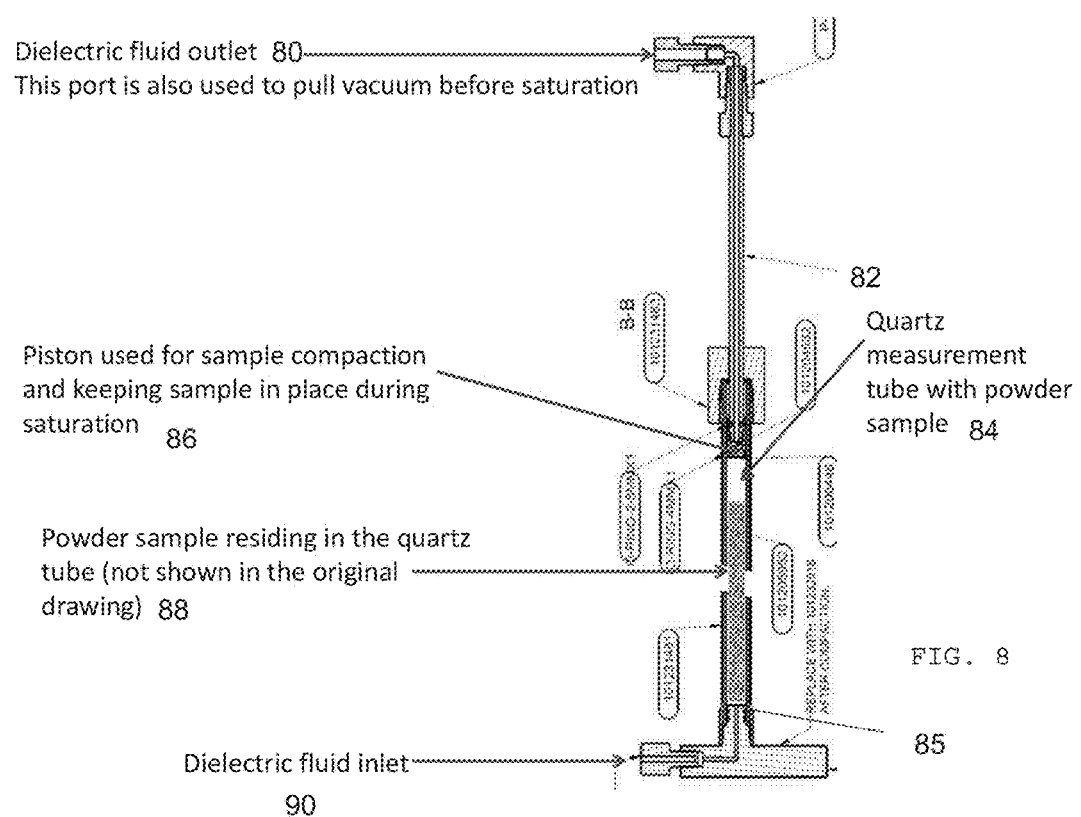
FIG. 8 shows a measurement cell for the resonator in FIG. 7 installed in a saturation/compaction apparatus.

To test the foregoing technique, rock powder was mixed in automixers to obtain substantially homogeneous samples. The sample was split in three or more equal parts. A portion of the dry powder was loaded in a measurement tube. The measurement tube may be installed in a compaction/saturation setup that is schematically represented at 82 in FIG. 8. The measurement tube 84 is closed at one end with a plug 85 and a movable piston 86 is inserted into the measurement tube 84 from the other end.

The piston 86 is lowered until it reaches the top of the powder 88 placed in the sample tube 84. For each sample exactly the same amount of powder 88 is placed in the sample tube 84 and the final piston 86 position is kept constant so that the powder 88 porosity is the same among all subsamples of the same rock powder.

Further, the sample tube 84 may be evacuated using through the top of the piston 86 through line 90 to avoid air bubbles in the liquid/powder mixture. Once sufficient vacuum is achieved an evacuation valve (not shown) is shut off and the required liquid is pumped through inlet 90 and the bottom plug 85 into the sample tube 84. As an example, a dielectric fluid outlet 80 may be used to pull vacuum before saturation. Several pore volumes of liquid may be pumped through the sample tube 84 until complete saturation is achieved.

Once the powder 88 is saturated the top piston 86 is removed and the sample tube 84 is placed in the dielectric resonator (FIG. 7). Next, measurement of the powder/liquid mixture permittivity is performed. To conduct subsequent measurements with a different saturating fluid, a new portion of the same prepared sample of rock powder is selected and the foregoing procedure may then be repeated with another fluid. In another example, the same powder sample can be used and the original saturating fluid can be substituted by another fluid in the compaction/flow apparatus (82 in FIG. 8) by pumping a sufficient amount of the other fluid through the sample.

There are several methods that can be used to calculate a powder matrix permittivity from liquid/powder measurements performed as described above.

For instance, the matrix permittivity can be calculated from a single permittivity measurement of a powder/liquid mixture using a mixing law and measurements of the powder porosity and liquid permittivity. The present example is based on the CRIM law, but any other mixing law can be applied:

$$\varepsilon_{matrix} = \left( \frac{\sqrt{\varepsilon_{mixture}} - \phi \sqrt{\varepsilon_{liquid}}}{1 - \phi} \right)^2 \qquad (14)$$

where $\varepsilon_{mixture}$ is the effective permittivity of the powder/liquid mixture, $\varepsilon_{liquid}$ is the permittivity of liquid and $\phi$ is the sample liquid-filled porosity. Only the real part of the permittivities or the complex permittivities can be utilized in the computation.

Figure 9:
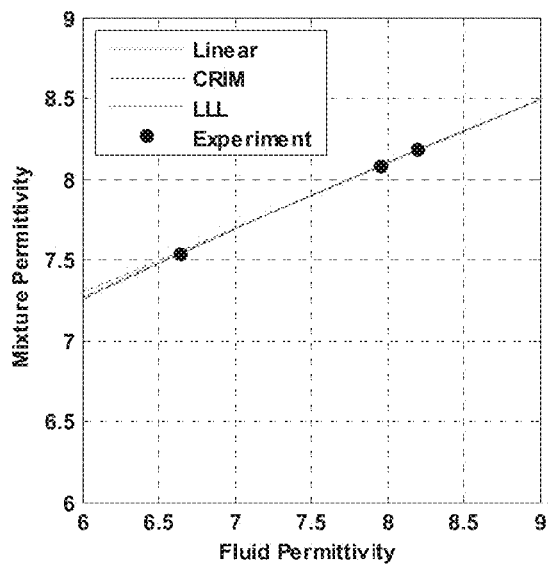
FIG. 9 shows a graph of various mixing laws fitted to experimental data obtained on dolomite powder saturated with three different liquids.
Figure 10:
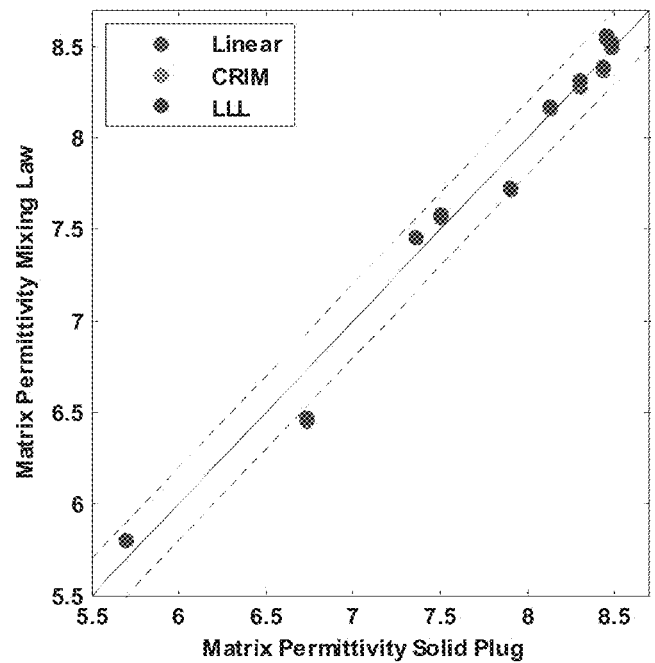
FIG. 10 shows a graph of a comparison of the matrix permittivity values determined from mixing law fitting and matrix permittivity values measured on solid rock samples.

The matrix permittivity may be calculated from simultaneous fitting of two or more measurements on liquid/powder mixtures using liquids with different permittivity values. Only the real part of the permittivities or the complex permittivities may be utilized in fitting. The present example is based on three mixing laws: Linear law, Complex Refractive Index law (CRIM) and Looyenga-Landau-Lifshits (LLL) law, but any other mixing law can be utilized. The powder liquid-filled porosity and the permittivities of the sample-saturating liquids were fixed at measured values. The powder matrix permittivity was the only parameter that was varied during curve fitting. An example of the fitting results to experimental data obtained on three powder/liquid mixtures is shown in FIG. 9. The three mixing laws provided similar fit and similar matrix permittivity values. The similarity between the mixing laws predictions is expected as the dielectric contrast between the saturating fluids and rock powders was small, which makes the choice of the mixing law less important. This approach was further tested on a range of powdered rock and mineral end-member samples. The test rocks were first cut into solid cylindrical plugs. The reference permittivity of the rock matrix on the rock cores was determined using the example methodology described above with reference to measurements of solid rock plug samples. These samples where further crushed into powder and the above described approach for powder measurements was applied. The comparison between the matrix permittivity obtained on powders and the matrix permittivity values measured on solid plugs is shown in FIG. 10. Good correspondence between both values is observed, with the standard deviation for permittivity values obtained with CRIM law fitting of 0.21.

Furthermore, using measurements on two or more liquid/powder mixtures using liquids with different permittivity, both the powder matrix permittivity and powder porosity can be determined by inversion if the powder porosity remains the same between the measurements using different liquids.

Figure 11:
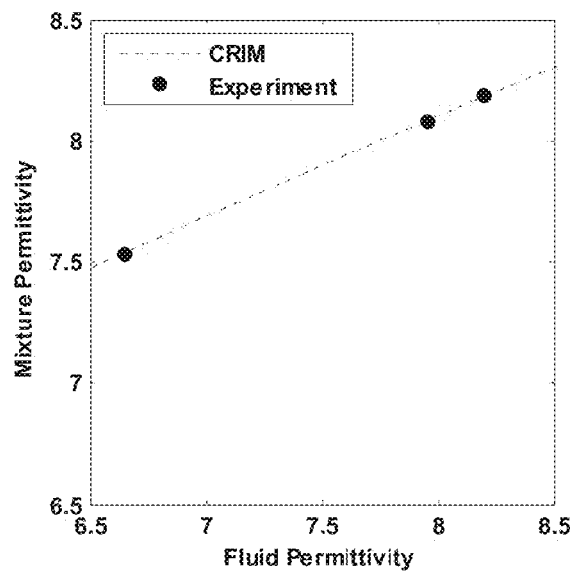
FIG. 11 shows a graph of CRIM matrix permittivity inversion on dolomite powder/liquid mixtures.
Figure 12:
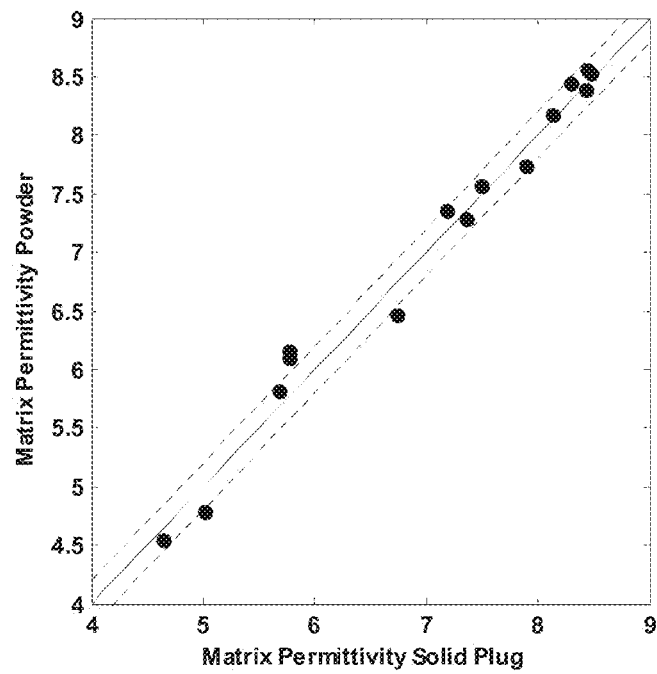
FIG. 12 shows a graph of a comparison of matrix permittivity determined with CRIM inversion with the matrix permittivity determined from solid rock samples.

The inversion approach in the present example uses the CRIM mixing law, but any other mixing law can be used. For each sample simultaneous inversion of three experimental data points was performed with the CRIM mixing law for both powder matrix permittivity and porosity values. The liquid permittivity was an input parameter to the inversion corresponding to its value at the measurement temperature. The inversion algorithm adjusted the powder matrix permittivity and porosity values so that a minimized misfit between the experimental data and the predicted permittivity of powder/liquid is minimized. CRIM inversion results for a series of measurements on a single sample is shown in FIG. 11 and illustrate a good fit to the data. Comparison of the matrix permittivity values inverted with the CRIM mixing law and the values obtained on plugs for a collection of test samples is shown in FIG. 12. The correspondence between the measured and the reference matrix permittivity values is good with the standard deviation being only 0.18. The inversion approach has an advantage of not requiring powder porosity as an input parameter.

3. Measurement of Mixed-Solid Composition Samples

Rock samples are often composed of multiple minerals and do not represent a single rock matrix composition. However, it is important to establish permittivity end-points for pure minerals as these values are required for dielectric well log interpretation.

An example methodology for determining permittivity values of individual mixture components uses measurements on a series of mixtures or rocks with variable mineralogical content. The methodology in the present example is based on the CRIM mixing law, but any other mixing law can be applied.

According to the CRIM law:

$$\varepsilon_{eff}^{1/2} = \sum_{n=1}^{N} V_n \varepsilon_n^{1/2} \quad (15)$$

Linear regression analysis may be used to investigate the influence of the mineralogical content of the rock on its effective permittivity. The imaginary part of the permittivity of most subsurface minerals associated with hydrocarbon production is small and will be omitted in the subsequent analysis.

A multiple linear regression analysis formulated in the equation (7) produces an estimate of $\varepsilon_n^{1/2}$ utilizing measurements of $\varepsilon_{eff}^{1/2}$ and $V_n$. The linear regression can be cast in the following matrix equation:

$$y = X\beta, \quad (16)$$

where the vector of measured variables y is defined as:

$$y = \begin{pmatrix} \varepsilon_1^{1/2} \\ \vdots \\ \varepsilon_N^{1/2} \end{pmatrix}, \quad (17)$$

the matrix X is $$X = \begin{pmatrix} V_{11} & \cdots & V_{1p} \\ \vdots & \ddots & \vdots \\ V_{N1} & \cdots & V_{Np} \end{pmatrix}, \quad (18)$$

and the parameter vector, β, takes the form of $$\beta = \begin{pmatrix} \beta_1 \\ \vdots \\ \beta_p \end{pmatrix}, \quad (19)$$

where $\beta_i = \varepsilon_{mi}^{1/2}$ for each mineral i.

The parameter vector was estimated with the ordinary least squares (OLS) method. The OLS method minimizes the sum of the squared residuals, and leads to a closed-form expression for the estimated value of the unknown parameter vector, $\hat{\beta}$:

$$\hat{\beta} = (X'X)^{-1}X'y \quad (20)$$

The linear regression analysis requires the inequality N>p to be satisfied, where N is the number of measurements and p is the number of parameters. This implies that there must be enough data available compared to the number of parameters to be estimated. The technique was demonstrated on seventeen powder samples to conduct regression on nine mineral fractions following Table 2.

The data was further renormalized so that the volume percent of the selected fractions would add up to 100% while maintaining the relative proportion of each fraction. The linear regression analysis on the reduced mineralogical dataset yields the parameter vector listed in Table 2.

TABLE 2

PARAMETER VECTOR ESTIMATE OBTAINED WITH OLS METHOD.

| Mineral | $\beta_i$ | $\beta_i^2$ | $\varepsilon_{mat}$ |
|---|---|---|---|
| Buddingtonite | 2.53 | 6.38 | — |
| Dawsonite* | 1.75 | 3.07 | — |
| Dolomite+ | 2.64 | 6.97 | 6.8 |
| Feldspars+ | 2.60 | 6.76 | 4.4-6.0 |
| Clay+ | 2.37 | 5.64 | ~5.8 |
| Kerogen | 1.80 | 3.23 | — |
| Nacholite* | 2.83 | 7.99 | — |
| Pyrite* | 6.10 | 37.20 | — |
| Quartz | 2.19 | 4.79 | 4.65 |

*regression results may be unreliable due to small mineral content
+lumped mineral According to the CRI law the square of the parameter vector values, $\beta_i^2$, correspond to the mineral permittivity values. Table 2 lists parameter vector estimates and published values of the matrix permittivity for some of the minerals. For example, $\beta_i^2$ for quartz, clay and dolomite are close to the published permittivity values. Although "dolomite" and "clay" are lumped minerals they contain predominantly dolomite and illite minerals. The $\beta^2$ value for "feldspars" is somewhat higher than expected values, which could be due to presence of multiple minerals in this lumped fraction. Three minerals (dawsonite, nacholite, and pyrite) were present in small quantities and the obtained regression results may be unreliable due to low content.

4. Permittivity Measurements at Variable Temperature

The algorithm for determining permittivity of powdered samples described above makes use of permittivity measurements on powders saturated with two or more fluids with different permittivities. In practice using the foregoing method requires either saturating the same powder with several liquids sequentially or using several portions of the same sample for saturation with different liquids.

Each saturation cycle may take several hours. In addition, if several different sample portions are used, additional sample powder may be required. For practical applications it is desirable to reduce measurement time and sample amount requirements. Both of such objectives may be achieved by making permittivity measurements on powder/liquid mixtures at variable temperatures.

Figure 13:
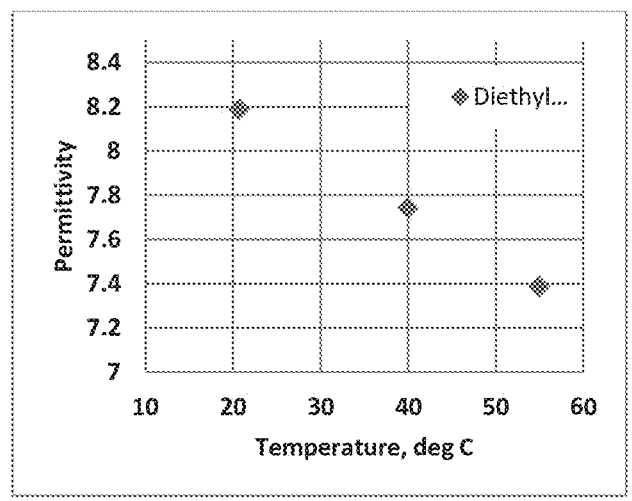
FIG. 13 shows a graph of diethyl oxalate permittivity dependence on temperature.

Experimental data on the dependence of the permittivity of diethyl oxalate with respect to temperature is shown in FIG. 13. It is evident that increase in temperature leads to a significant reduction in the fluid permittivity. Thus instead of sequentially saturating a powdered sample with several liquids with different permittivities it is possible to use a single fluid by conducting measurements at different temperatures such that permittivity of the saturating fluid changes in a known way. This approach eliminates the necessity of repeating the saturation procedure multiple times and/or splitting the sample into portions and, therefore, may significantly reduce sample amount requirements and preparation time.

The foregoing procedure was tested on the same powders and showed that measurements at two or more temperatures may enable determination of the powder permittivity using described above approach. For example, measurements at 20° C., 55° C. and 80° C. were used in testing. The optimum fluid permittivity at room temperature (approximately 25° C.) should be slightly higher than the expected permittivity of the powder. For example, for a carbonate powder sample diethyl oxalate or malonate was tested, while for siliciclastic samples diethyl suberate was tested.

Permittivity of rock minerals determined using the methods described herein may enable more accurate determination of wellbore formation dielectric properties. More accurate determination of formation dielectric properties may enable more accurate estimation of water filled pore volume in such formations.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining permittivity of a rock formation mineral matrix, comprising:
saturating a known volume of a sample obtained from well logging of the rock formation with at least two different dielectric materials having different permittivities, wherein the sample comprises a powder of the rock formation mineral matrix, wherein the saturated sample has a known total volume;
measuring a permittivity of the sample using a dielectric resonator;
determining a fractional volume of pore space in the sample as a part of well logging analysis; and
using a mixing law and the permittivities of the at least two dielectric materials to determine the permittivity of the rock formation mineral matrix from the measured permittivity of the sample, wherein the permittivity of the rock formation mineral matrix at least depends on the permittivity of the sample, the fraction volume of the pore space in the sample, and the permittivities of the at least two dielectric materials.

2. The method of claim 1 wherein the mixing law comprises at least one of the Maxwell-Garnett mixing formula, the Effective Medium Approximation, Polder-van Santen mixing formula, the Arithmetic Average (Volumetric) Mixing Formula, the Harmonic Average Mixing Formula, the Complex Refractive Index Formula, the Looyenga-Landau-Lifshiz Mixing Formula, and Lichtenecker's Mixing Formula.

3. The method of claim 1 wherein the at least two dielectric material comprise a liquid.

4. The method of claim 3 wherein the liquid comprises diethyl liquid.

5. The method of claim 3 wherein the liquid is pumped into the sample so that the total sample volume is known, and the sample is subjected to vacuum to extract any trapped gases therefrom.

6. The method of claim 1 wherein the rock matrix permittivity and the fractional volume of pore space in the sample are determined by inversion of the sample permittivity measurement.

7. The method of claim 6 wherein the at least two different dielectric materials have permittivities at a first value being at an upper end of a useful measurement range and, respectively a second value at a lower end of a useful range.

8. The method of claim 7 further comprising mixing the at least two different dielectric materials in proportions selected to provide a predetermined permittivity.

9. The method of claim 8 wherein the rock matrix permittivity is determined by combining measurements of saturated sample permittivity using a plurality of different proportions of the at least two different dielectric materials.

10. The method of claim 8 wherein using the mixing law and the permittivities of the at least two dielectric materials to determine the permittivity of the rock formation mineral matrix comprises using the mixing law and the predetermined permittivity to determine the permittivity of the rock formation mineral matrix.

11. The method of claim 1 wherein the mixing law comprises the Looyenga-Landau-Lifshiz Mixing Formula.

12. The method of claim 1 wherein the mixing law comprises the Complex Refractive Index Formula.

13. The method of claim 1 further comprising mixing the at least two different dielectric materials in proportions selected to provide a predetermined permittivity of the fluid.

14. The method of claim 1 wherein the at least two dielectric materials comprise three dielectric materials.

15. The method of claim 1 further comprising mixing the at least two different dielectric materials in proportions selected to provide a predetermined permittivity.

16. The method of claim 15 wherein the using the mixing law and the permittivities of the at least two dielectric materials to determine the permittivity of the rock formation mineral matrix comprises using the mixing law and the predetermined permittivity to determine the permittivity of the rock formation mineral matrix.

17. The method of claim 1 wherein determining the fractional volume of pore space comprises determining the fractional volume by inversion of the sample permittivity measurement.

18. The method of claim 1 wherein:
saturating the sample with the at least two different dielectric materials comprises:
saturating the sample with a first dielectric material of the at least two dielectric materials at a first time; and saturating the sample with a second dielectric material of the at least two dielectric materials at a second time different than the first time; and measuring the permittivity of the sample comprises:

measuring a first permittivity of the sample saturated with the first dielectric material; and measuring a second permittivity of the sample saturated with the second dielectric material.

19. The method of claim 18 further comprising curve fitting the first and second permittivities to the permittivities of the at least two dielectric materials using the mixing law.

20. The method of claim 19 further comprising curve fitting the first and second permittivities to the permittivities of the at least two dielectric materials using a second, different mixing law.

21. The method of claim 18 wherein saturating the sample with the second dielectric material comprises saturating the sample with the second dielectric material after the sample has been saturated with the first dielectric material.

\* \* \* \* \*